United States Patent
Ideta et al.

(10) Patent No.: US 10,392,599 B2
(45) Date of Patent: Aug. 27, 2019

(54) METHOD FOR NON-FREEZE LOW-TEMPERATURE PRESERVATION OF MAMMALIAN EMBRYO OR FERTILIZED EGG

(75) Inventors: Atsushi Ideta, Kato-gun (JP); Yoshito Aoyagi, Kato-gun (JP)

(73) Assignee: NATIONAL FEDERATION OF AGRICULTURAL COOPERATIVE ASSOCIATIONS, Tokyo (JP)

( * ) Notice: Subject to any disclaimer, the term of this patent is extended or adjusted under 35 U.S.C. 154(b) by 0 days.

(21) Appl. No.: 14/423,032

(22) PCT Filed: Aug. 21, 2012

(86) PCT No.: PCT/JP2012/071079
§ 371 (c)(1),
(2), (4) Date: Feb. 20, 2015

(87) PCT Pub. No.: WO2014/030211
PCT Pub. Date: Feb. 27, 2014

(65) Prior Publication Data
US 2015/0218511 A1 Aug. 6, 2015

(51) Int. Cl.
*C12N 5/073* (2010.01)
*A01N 1/02* (2006.01)
(Continued)

(52) U.S. Cl.
CPC ......... *C12N 5/0604* (2013.01); *A01N 1/0221* (2013.01); *C12M 21/06* (2013.01); *C12M 23/08* (2013.01)

(58) Field of Classification Search
None
See application file for complete search history.

(56) References Cited

U.S. PATENT DOCUMENTS

| 2003/0077655 A1* | 4/2003 | Rees | A01N 1/02 |
| | | | 435/7.1 |
| 2010/0190248 A1* | 7/2010 | Critser | A01N 1/0221 |
| | | | 435/366 |

FOREIGN PATENT DOCUMENTS

| JP | 64-72742 A | 3/1989 |
| JP | 2002-233356 A | 8/2002 |
| JP | 2010-248160 A | 11/2010 |

OTHER PUBLICATIONS

Gow, Analytica Chimica Acta 432: 143-149 (2001).*
(Continued)

*Primary Examiner* — Erin M. Bowers
(74) *Attorney, Agent, or Firm* — Birch, Stewart, Kolasch & Birch, LLP

(57) ABSTRACT

Disclosed is a novel means which enables satisfactory preservation of embryos and fertilized eggs in the non-frozen state for a longer period than conventional means, which novel means also achieves high hatching ability and a high conception rate of the embryos after the preservation. The method for preserving a mammalian embryo(s) or fertilized egg(s) of the present invention comprises immersing a mammalian embryo(s) or fertilized egg(s) in a medium containing 20 to 80% (v/v) serum and 10 to 100 mM Good's buffer, and storing the embryo(s) or fertilized egg(s) at non-freezing low temperature. The preservative solution for a mammalian embryo(s) or fertilized egg(s) of the present invention essentially consists of a medium containing 20 to 80% (v/v) serum and 10 to 100 mM Good's buffer. The Good's buffer is preferably HEPES.

15 Claims, 1 Drawing Sheet

Specification includes a Sequence Listing.

(51) Int. Cl.
*C12M 3/00* (2006.01)
*C12M 1/24* (2006.01)

(56) References Cited

OTHER PUBLICATIONS

Smith et al., Theriogenology 25(1): 199 (1986).*
Lindner et al., Theriogenology 23(1): 202 (1985).*
Baguisi et al., "Hypothermic Storage of Sheep Embryos with Antifreeze Proteins: Development In Vitro and In Vivo," Theriogenology (1997), vol. 48, pp. 1017-1024.
Lindner, G. M. and D. E. Ellis, "Refrigeration of Bovine Embryos," Theriogenology (Jan. 1985) vol. 23, No. 1, p. 202.
Massip et al., "Calving outcome following transfer of embryos produced in vitro in different conditions," Animal Reproduction Science (1996), vol. 44, pp. 1-10.
Ono et al., "Collection, conservation and transplantation of fertilized eggs of cattle by use of Eagle's minimum essential medium supplemented with Trisaminomethane," Animal Husbandry (1986), vol. 40, No. 3, pp. 65 and 66, with partial English translation.
Tsuchiya et al., "Short-term Preservation of Mouse Oocytes at 5° C.," Exp. Anim. (2001), vol. 50, No. 5, pp. 441-443.
Yamaguchi et al., "Short-term Low-temperature Preservation of Mouse Morulae," The Japanese Society Zootechnical Science Annual Meeting (2002), p. 106, V28-22, Abstracts, with English translation.

* cited by examiner

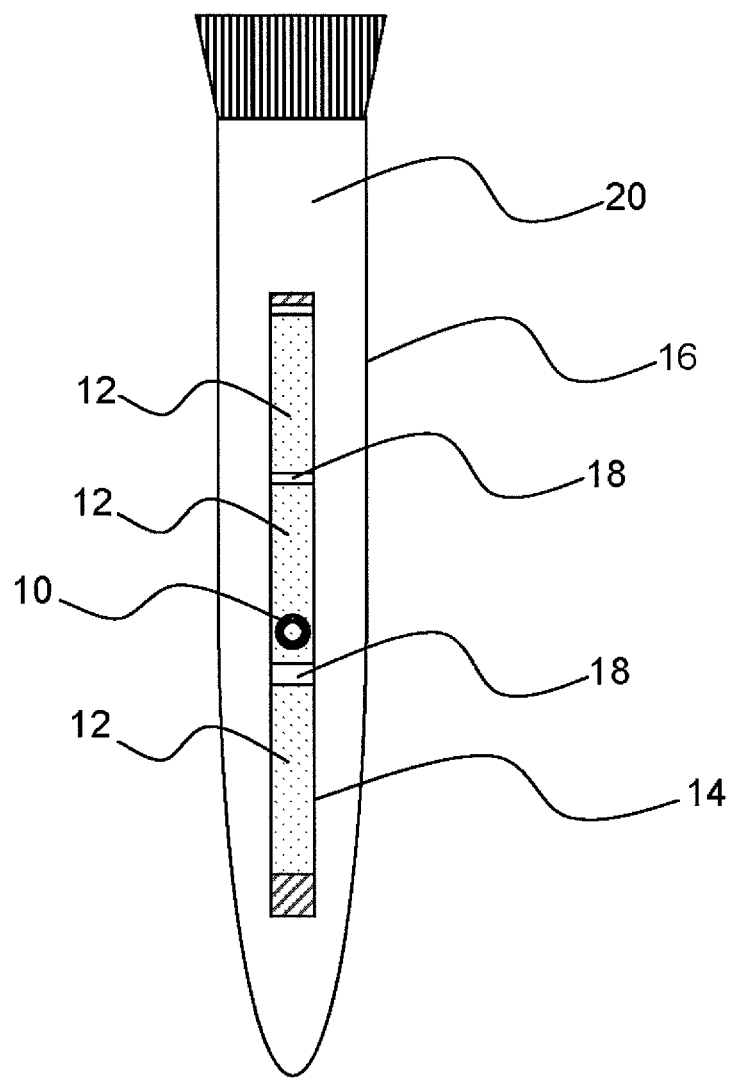

SEQUENCE LISTING

```
<160> NUMBER OF SEQ ID NOS: 2

<210> SEQ ID NO 1
<211> LENGTH: 201
<212> TYPE: DNA
<213> ORGANISM: Zoarces elongatus Kner
<220> FEATURE:
<221> NAME/KEY: CDS
<222> LOCATION: (1)..(201)

<400> SEQUENCE: 1 aac cag gag tcc gtg gtg gcc gcc gtt ctg atc ccc ata aat act gcc      48
Asn Gln Glu Ser Val Val Ala Ala Val Leu Ile Pro Ile Asn Thr Ala
1               5                   10                  15 ctg act gtg ggg atg atg acg aca cgg gtg gtc tcc cca acg ggc atc      96
Leu Thr Val Gly Met Met Thr Thr Arg Val Val Ser Pro Thr Gly Ile
            20                  25                  30 ccc gcc gag gac att ccc cga tta atc tca atg caa gtg aac cag gta     144
Pro Ala Glu Asp Ile Pro Arg Leu Ile Ser Met Gln Val Asn Gln Val
        35                  40                  45 gtg ccg atg ggc aca acc ctc atg cca gac atg gtg aaa ggg tac gcc     192
Val Pro Met Gly Thr Thr Leu Met Pro Asp Met Val Lys Gly Tyr Ala
    50                  55                  60 ccg gct tag                                                          201
Pro Ala
65

<210> SEQ ID NO 2
<211> LENGTH: 66
<212> TYPE: PRT
<213> ORGANISM: Zoarces elongatus Kner
```

```
<400> SEQUENCE: 2

Asn Gln Glu Ser Val Val Ala Ala Val Leu Ile Pro Ile Asn Thr Ala
1               5                   10                  15

Leu Thr Val Gly Met Met Thr Thr Arg Val Val Ser Pro Thr Gly Ile
            20                  25              30

Pro Ala Glu Asp Ile Pro Arg Leu Ile Ser Met Gln Val Asn Gln Val
        35              40                  45

Val Pro Met Gly Thr Thr Leu Met Pro Asp Met Val Lys Gly Tyr Ala
    50              55                  60

Pro Ala
65
```

METHOD FOR NON-FREEZE LOW-TEMPERATURE PRESERVATION OF MAMMALIAN EMBRYO OR FERTILIZED EGG

TECHNICAL FIELD

The present invention relates to a method and a preservative solution for preserving a mammalian embryo(s) or fertilized egg(s) at non-freezing low temperature.

BACKGROUND ART

Not less than 60,000 bovine embryos are distributed per year in Japan. The demand for bovine embryos is increasing year by year in North America, South America, Europe and Asia. Thus, researches on cryopreservation of bovine embryos are being carried out worldwide, and development of a number of slow freezing methods and rapid freezing methods has realized relatively stable conception rates. However, the conception rate which can be achieved at the current technological level is only about 50%, and no significant improvement in the conception rate has been made during the last 20 or more years. This might indicate that cryopreservation of mammalian embryos has reached a certain technological limit.

Embryos resistant to damage caused by freezing/thawing are limited to high-quality embryos. Production of a plurality of embryos by superovulation treatment often results in obtaining only low-quality embryos due to various factors (for example, bad physical condition of the donor cattle or low vitality of the donated sperm). Nevertheless, these low-quality embryos can also be implanted into the uteri of recipient cattle to produce calves if the embryos have not undergone freezing treatment.

If there is any method available that allows survival of bovine embryos collected from donor cattle in the non-frozen state for a short period while suppressing their growth, embryos that have not suffered from injury by freezing/thawing can be very efficiently used for production of calves by utilization of transportation means such as home delivery services. Moreover, in cases where there is a time lag of several days between the estrous cycles of the donor cattle and the recipient cattle, the timing of implantation can be adjusted according to the estrous cycle of the recipient cattle. Furthermore, development of such a method for preserving embryos will eliminate the necessity of liquid nitrogen or an expensive refrigeration equipment such as a deep freezer. That is, preservation of embryos in a household refrigerator will become possible.

It has been reported that the limit of the period of non-freezing preservation is 3 days in the case of bovine embryos (Non-patent Document 1), and 4 days in the case of ovine embryos (Non-patent Document 2). A thermal hysteresis protein (Nfe8) and thermal hysteresis-like proteins Nfe11 and Nfe6, which are found in a fish species *Zoarces elongatus* Kner, have been reported to exert a cell life prolonging function under low-temperature conditions (Patent Document 1), and their practical use as cell life prolonging agents has been expected.

The animal species which have been studied for non-freezing low-temperature preservation include various species such as mouse, pig, sheep, cattle, and rare species. The properties of embryos are largely different among the animal species. Thus, components effective for embryo preservation, and mixing ratios and effective concentration ranges of these components, are also largely different among the species, and therefore components for the preservative solution need to be carefully examined for each animal species. The method of preservation of bovine embryos at non-freezing low temperature has long been studied from the viewpoints of improvement of the conception rate, estrus synchronization between the donor cattle and the recipient cattle, and utilization of low-quality embryos. However, no effective preservation method has been developed so far.

Under such circumstances, development of a preservative solution for mammalian embryos which not only enables more effective protection or preservation of mammalian embryos at non-freezing low temperature to prolong their life, but also achieves maintenance of hatching ability and a high conception rate, has been demanded. Similarly, development of a method for preserving mammalian embryos which not only enables their preservation for the number of days required for transportation, but also realizes their preservation and transportation using small general-purpose equipment or a container that consumes less energy, has been strongly demanded.

PRIOR ART DOCUMENTS

Patent Document

Patent Document 1: JP 2010-248160 A

Non-Patent Documents

Non-patent Document 1: Lindner G M and Ellis D E. Refrigeration of bovine embryos. Theriogenology 1985; 23:202.

Non-patent Document 2: Baguisi A, Arav A, Crosby T F, Roche J F, Boland M P. Hypothermic storage of sheep embryos with antifreeze proteins: development in vitro and in vivo. Theriogenology 1997; 48:1017-1024.

SUMMARY OF THE INVENTION

Problems to be Solved by the Invention

Accordingly, an object of the present invention is to provide means which enables satisfactory preservation of mammalian embryos or fertilized eggs in the non-frozen state for a longer period than conventional means, which novel means also achieves high hatching ability and conception rate of the embryo after the preservation.

Means for Solving the Problems

As a result of intensive study, the present inventors discovered that use of a combination of serum and a Good's buffer at specific concentrations enables long-term preservation of mammalian embryos in the non-frozen state without using a cell life prolonging peptide such as Nfe11, and that use of HEPES produces an especially favorable effect which enables achievement of very high survival and conception rates even in the case where the embryos are preserved in the non-frozen state for a period of as long as 7 days, thereby completing the present invention.

That is, the present invention provides a method for preserving a mammalian embryo(s) or fertilized egg(s), the method comprising immersing a mammalian embryo(s) or fertilized egg(s) in a medium containing 20 to 80% (v/v) serum and 10 to 100 mM Good's buffer, and storing the embryo(s) or fertilized egg(s) at non-freezing low temperature. The present invention also provides a preservative solution for a mammalian embryo(s) or fertilized egg(s), essentially consisting of a medium containing 20 to 80% (v/v) serum and 10 to 100 mM Good's buffer.

Effect of the Invention

By the present invention, mammalian embryos and fertilized eggs can be preserved in the non-frozen state for a longer period compared to conventional methods, without use of a special component as a preservative solution component. In the case where HEPES is used as the Good's buffer, an especially favorable effect can be obtained, and very high survival and conception rates can be achieved even after preservation of mammalian embryos in the non-frozen state for a period of as long as 7 days. Since non-freezing preservation of mammalian embryos or fertilized eggs for 7 days has not yet been realized, the present invention significantly contributes to breeding of superior livestock as described below.

Conventionally, fertilized livestock eggs for commercial purposes (for example, 7-day-old embryos (morulae) of Japanese Black Cattle) are enclosed in cylinders called straws having a diameter of about 2 mm and a length of about 15 cm, in a state where the eggs are immersed in a preservative solution, and commercially distributed in a state where the straws are immersed in liquid nitrogen. In the state where the straws are immersed in liquid nitrogen, their air transportation is prohibited by the Civil Aeronautics Law, and the straws are therefore transported to consumers (animal husbandry associations and livestock farmers) by ground transportation by freight train or truck. Thus, there is a problem of an increase in the transportation cost, which leads to a rise in the price of fertilized livestock eggs. By the present invention, long-term non-freezing low-temperature preservation is possible, and fertilized eggs (embryos) can be transported in a state where the eggs are contained in a small cold box or the like, without use of liquid nitrogen. This allows transportation by airplane, and enables low-cost and more rapid transportation of fertilized eggs to distant places. In cryopreservation of embryos, the embryos are physically damaged during freezing and thawing. On the other hand, in non-freezing preservation, there is no such a risk, and an improved conception rate can be expected.

Conventionally, in production of fertilized bovine eggs for commercial purposes, about 20% of bovine embryos are discarded because of disagreement between the estrous cycles of the donor cattle and the recipient cattle, or of low quality. By enabling preservation of livestock embryos in the non-frozen state, effective utilization of low-quality embryos that are not resistant to physical damage caused by freezing/thawing becomes possible. Moreover, even in cases where there is a time lag of several days between the estrous cycles of the donor and the recipient, it becomes possible to adjust the timing of implantation depending on the estrous cycle of the recipient. The present invention enables effective utilization of livestock embryos that have been discarded because of the disagreement between the estrous cycles, or of low quality.

According to the method of the present invention, embryos or fertilized eggs immersed in a preservative solution can be used without washing, and can be implanted into the uteri of recipient animals together with the preservative solution. The present inventors previously found that, by using a special peptide (mature Nfel1) having a cell life prolonging effect in combination with about 20 to 50% (v/v) serum, bovine embryos can be preserved at non-freezing low temperature for up to 5 days. In cases where a peptide having cell life prolonging activity is industrially used, the peptide expressed in E. coli or the like by genetic engineering techniques and then purified is usually used. However, since implantation of embryos or fertilized eggs together with a preservative solution containing a recombinant peptide into the uteri of recipient animals cannot be carried out until the safety of the recombinant peptide is sufficiently evaluated, the embryos or fertilized eggs need to be washed before the implantation. Since in the present invention a recombinant peptide is not used, embryos after preservation at low temperature can be implanted into recipient parents as they are without washing the embryos. This method is more simple, and can reduce physical damage to the embryos.

BRIEF DESCRIPTION OF THE DRAWINGS

FIG. 1 is a diagram illustrating a specific example in which a bovine embryo is enclosed in a straw using the preservative solution of the present invention to carry out non-freezing low-temperature preservation.

MODE FOR CARRYING OUT THE INVENTION

In the method of the present invention, a mammalian embryo(s) or fertilized egg(s) is(are) immersed in a medium containing serum and a Good's buffer at specific concentrations, and the embryo(s) or fertilized egg(s) is(are) stored at non-freezing low temperature.

Good's buffers have common characteristics: for example, they are less likely to pass through biomembranes; they are highly soluble in water; and they have low ability to form complexes with metal ions. Good's buffers are considered to have actions to stabilize the pH of the medium during preservation of embryos or fertilized eggs, and to protect the cell membrane of the embryos or fertilized eggs during non-freezing low-temperature preservation. As described in the Examples below, it is assumed that the effect of Good's buffers to prolong the life of embryos and fertilized eggs during non-freezing low-temperature preservation is not significantly dependent on the stabilization per se of the pH of the medium (preservative solution) during the preservation, but is based on a cell-membrane-protecting action other than the pH stabilization.

Specific examples of the buffers known as Good's buffers include the following:

MES [2-Morpholinoethanesulfonic acid],
Bis-Tris [Bis(2-hydroxyethyl)iminotris(hydroxymethyl)methane],
ADA [N-(2-Acetamido)iminodiacetic acid],
PIPES [Piperazine-1,4-bis(2-ethanesulfonic acid)],
ACES [N-(2-Acetamido)-2-aminoethanesulfonic acid],
MOPSO [2-Hydroxy-3-morpholinopropanesulfonic Acid],
BES [N,N-Bis(2-hydroxyethyl)-2-aminoethanesulfonic acid],
MOPS [3-Morpholinopropanesulfonic acid],
TES [N-Tris(hydroxymethyl)methyl-2-aminoethanesulfonic acid],
HEPES [4-(2-hydroxyethyl)-1-piperazineethanesulfonic acid],
DIPSO [3-[N,N-Bis(2-hydroxyethyl)amino]-2-hydroxy-1-propanesulfonic acid],
TAPSO [3-(N-tris[Hydroxymethyl]methylamino)-2-hydroxypropanesulfonic acid],
POPSO [Piperazine-1,4-bis(2-hydroxypropanesulfonic acid)],
HEPPSO [N-(Hydroxyethyl)piperazine-N'-2-hydroxypropanesulfonic acid], EPPS [3-[4-(2-Hydroxyethyl)-1-piperazinyl]propanesulfonic acid],
Tricine [N-[Tris(hydroxymethyl)methyl]glycine],
Bicine [N,N-Bis(2-hydroxyethyl)glycine],
TAPS [N-Tris(hydroxymethyl)methyl-3-aminopropanesulfonic acid],
CHES [N-Cyclohexyl-2-aminoethanesulfonic acid],
CAPSO [N-cyclohexyl-2-hydroxyl-3-aminopropanesulfonic acid], and
CAPS [N-Cyclohexyl-3-aminopropanesulfonic acid].

In the present invention, any of these known Good's buffers can be used. It is said that the optimum pH for cells is usually 6.8 to 7.2, and that cells can be ideally maintained within this pH range. Thus, a Good's buffer that can exert a favorable buffer capacity in the neutral range (pH 6 to 8) at non-freezing low temperature can be preferably used. Examples of the Good's buffer that can be favorably used include at least one selected from MES, Bis-Tris, ADA, PIPES, ACES, MOPSO, BES, MOPS, TES, HEPES, DIPSO, TAPSO, POPSO, HEPPSO, EPPS, Tricine, Bicine, and TAPS; or at least one selected from HEPES, PIPES, and MOPS. In the present invention, HEPES is especially preferably used. As a Good's buffer, a single kind of Good's buffer or a combination of 2 or more kinds of Good's buffers may be used.

The serum concentration (final concentration) in the medium is 20 to 80% (v/v), and may be, for example, 25 to 80% (v/v), 30 to 80% (v/v), 35 to 80% (v/v), 40 to 80% (v/v), 45 to 80% (v/v), 20 to 60% (v/v), 25 to 60% (v/v), 30 to 60% (v/v), 35 to 60% (v/v), 40 to 60% (v/v), 45 to 60% (v/v), or 45 to 55% (v/v).

The Good's buffer concentration (final concentration) in the medium is 10 to 100 mM, and may be, for example, 12.5 to 100 mM, 15 to 100 mM, 20 to 100 mM, 22.5 to 100 mM, 12.5 to 80 mM, 15 to 80 mM, 20 to 80 mM, 22.5 to 80 mM, 20 to 60 mM, 22.5 to 60 mM, 20 to 55 mM, 22.5 to 55 mM, or 22.5 to 52.5 mM. In cases where HEPES is used alone, the HEPES concentration in the medium can be preferably selected within these concentration ranges. The concentration may be similarly selected also in cases where another Good's buffer is used. In cases where two or more kinds of Good's buffers are used in combination, the total concentration may be within these ranges.

However, in cases where the Good's buffer is used at low concentration even within the above-described ranges, it is preferred that the serum concentration be higher. For example, in cases where the Good's buffer is used at a concentration of less than 15 mM, the serum concentration is preferably not less than about 30% (v/v), e.g., not less than about 40% (v/v).

By using serum and a Good's buffer at the above-described concentrations in combination, a mammalian embryo or fertilized egg can be preserved at non-freezing low temperature for a long period. In the present invention, the survival rate, hatching rate, and the like of embryos or fertilized eggs after preservation at non-freezing low temperature can be improved without using a peptide having cell life prolonging activity, such as the one described in Patent Document 1.

The peptide having cell life prolonging activity (which may be hereinafter referred to as "cell life prolonging peptide") refers to a peptide which allows cells preserved in the presence of the peptide under non-freezing low temperature conditions to survive at a significantly higher rate when compared to cells preserved in the absence of the peptide. Specific examples of the peptide include the Nfe11 protein described also in Patent Document 1. The present inventors previously discovered that use of a combination of mature Nfe11 and about 20 to 50% (v/v) serum enables preservation of bovine embryos at non-freezing low temperature for up to 5 days, and applied for a patent. Mature Nfe11 is a peptide composed of a 66-residue amino acid sequence formed by removal of the 22-residue secretory signal sequence in the N-terminal side of the precursor Nfe11 protein. Its amino acid sequence is shown in SEQ ID NO:2. SEQ ID NO:1 is the base sequence of cDNA encoding mature Nfe11. The "peptide having cell life prolonging activity" includes not only the peptide composed of the same amino acid sequence as the amino acid sequence of SEQ ID NO:2, but also a peptide composed of an amino acid sequence derived from the amino acid sequence of SEQ ID NO:2 by substitution, deletion, insertion and/or addition of a small number (e.g., 1 to several, 2 to 5, or 2 to 3) of the amino acid residues and having a homology of not less than 80%, for example, not less than 85%, not less than 90%, not less than 95%, or not less than 98% to the original amino acid sequence shown in SEQ ID NO:2, as long as such a peptide has a cell life prolonging activity.

Whether a peptide has cell life prolonging activity or not can be evaluated by, for example, incubating cells in the presence of the peptide and investigating whether or not survival of the cells is significantly prolonged when compared to control cells incubated in the absence of the peptide. The evaluation can be carried out by, for example, a method in which the survival rate is measured using a combination of a live cell staining fluorescent dye (e.g., Calcein-AM) and a dead cell staining fluorescent dye (e.g., propidium iodide) (De Clerck et al., Journal of Immunological Methods, 1994, 172(1), pp. 115-124; Nicoletti et al., Journal of Immunological Methods, 1991, 139(2), pp. 271-279), or a method in which the survival rate of cells is measured by quantifying cell damage (i.e., damage of the cell membrane) using the level of lactate dehydrogenase (LDH) as an indicator (T. Decker and M. L. L. Matthes, Journal of Immunological Methods, 1988, 115(1), pp. 61-69).

In the present invention, since the long-term preservation at non-freezing low-temperature is achieved by a combination of serum and a Good's buffer at specific concentrations, there is no need to add a peptide having cell life prolonging activity to the medium. An example of the mode of the method of the present invention is a method in which a mammalian embryo or fertilized egg is immersed in a medium which contains 20 to 80% (v/v) serum and 10 to 100 mM Good's buffer but contains neither (a) nor (b) described below, and the embryo or fertilized egg is then stored at non-freezing low temperature.

(a) The peptide whose amino acid sequence is shown in SEQ ID NO:2

(b) A peptide having an identity of not less than 80% to the amino acid sequence shown in SEQ ID NO:2 and having cell life prolonging activity.

Specific examples of the serum used in the present invention include bovine serum, pig serum, goat serum, and horse serum. Bovine serum is preferably used, but not limited thereto. Bovine serum may be any of fetal bovine serum, calf serum, and adult bovine serum.

The embryo(s) or fertilized egg(s) preserved by the method of the present invention is(are) not limited, and preferably an embryo(s) or fertilized egg(s) of livestock such as cattle, pig, goat, or horse. The method of the present invention can be especially preferably applied to a bovine embryo(s) or fertilized egg(s). The method of the present invention is applicable either to a fertilized egg before the beginning of cleavage or to a fertilized egg after the beginning of cleavage (i.e. embryo).

The medium used in the method of the present invention may be a medium commonly used for culturing mammalian embryos. Specific examples of commercially available media that can be used for culturing mammalian embryos include, but are not limited to, the following media. It should be noted that the concentrations of the components described below are merely examples in representative commercially-available products, and not limited to the specific examples described below.

<Medium 199>

Composition: 200 mg/L calcium chloride, 0.7 mg/L Iron (III) nitrate nonahydrate, 400 mg/L potassium chloride, 97.67 mg/L magnesium sulfate, 6.1 to 6.8 g/L sodium chloride, 2.2 g/L sodium hydrogen carbonate, 1 mM sodium dihydrogen phosphate (non-hydrate or monohydrate), 10 mg/L adenine sulfate, 1 mg/L adenosine-5-triphosphate, 0.2 mg/L adenosine-5-phosphate, 0.2 mg/L cholesterol, 0.5 mg/L deoxyribose, 1 g/L D-glucose, 0.05 mg/L reduced glutathione, 0.3 mg/L guanine hydrochloride, 0 mM or 25 mM HEPES (optional component), 0.4 g/L sodium hypoxanthine, 20 g/L Phenol Red, 0.5 mg/L ribose, 50 mg/L sodium acetate, 0.3 mg/L thymine, 20 mg/L Tween 80, 0.3 mg/L uracil, 0.34 mg/L sodium xanthine, 25 mg/L L-alanine, 70 mg/L L-arginine hydrochloride, 30 mg/L L-aspartic acid, 0.1 mg/L L-cysteine hydrochloride monohydrate, 26 mg/L L-cystine dihydrochloride, 75 mg/L L-glutamic acid, 50 mg/L glycine, 21.88 mg/L L-histidine hydrochloride monohydrate, 10 mg/L L-hydroxyproline, 40 mg/L L-isoleucine, 60 mg/L L-leucine, 70 mg/L L-lysine hydrochloride, 15 mg/L L-methionine, 25mg/L L-phenylalanine, 40 mg/L L-proline, 25 mg/L L-serine, 30 mg/L L-threonine, 10 mg/L L-tryptophan, 58 mg/L disodium L-tyrosine dihydrate, 25 mg/L L-valine, 0.05 mg/L ascorbic acid, 0.01 mg/L α-tocopherol phosphate, 0.01 mg/L d-biotin, 0.1 mg/L calciferol, 0.01 mg/L calcium D-pantothenate, 0.5 mg/L choline chloride, 0.01 mg/L folic acid, 0.05 mg/L i-inositol, 0.01 mg/L menadione, 0.025 mg/L nicotinic acid, 0.025 mg/L niacinamide, 0.05 mg/L para-aminobenzoic acid, 0.025 mg/L pyridoxal hydrochloride, 0.025 mg/L pyridoxine hydrochloride, 0.01 mg/L riboflavin, 0.01 mg/L thiamine hydrochloride, and 0.1 mg/L vitamin A.

<CR1aa Medium as Modified Medium 199>

Composition: 6.653 g/L sodium chloride, 0.233 g/L potassium chloride, 2.200 g/L sodium bicarbonate, 0.545 g/L calcium lactate, 0.044 g/L sodium pyruvate, 0.146 g/L L-glutamine, 20 mL/L MEM essential amino acid solution, 10 mL/L MEM non-essential amino acid solution, and 0.2 to 0.5% bovine serum albumin.

<HP-M199 Medium>

Composition: the same composition as medium 199 except that Tween 80 and para-aminobenzoic acid are not contained; HEPES is not contained.

In addition, a medium commonly used for culturing mammalian embryos may be mixed with one or more of other media such as BME medium, CMRL1066 medium, MEM medium, NCSU medium, and their modified media, to provide the medium for use. In cases where a commercially available medium already containing a Good's buffer and/or serum is used, the total concentration(s), including the concentration of this Good's buffer and/or the concentration of this serum, may be within the above-described concentration range(s) of Good's buffer and/or serum.

To the medium, an additive(s) such as an antioxidant(s) and/or stabilizer(s) may be added, if necessary. Examples of such components include phosphate salts, citrate salts, pyruvate salts, and other organic acids; antioxidants (e.g., SOD, vitamin E, and glutathione); pH adjusters (e.g., hydrochloric acid, acetic acid, and sodium hydroxide); low-molecular-weight polypeptides; hydrophilic polymers (e.g., polyvinylpyrrolidone); amino acids (e.g., glycine, glutamine, asparagine, arginine, and lysine); vitamins (e.g., vitamin A, vitamin Bs, vitamin C, vitamin Ds, biotin, folic acid); monosaccharide, disaccharide, and polysaccharide compounds (including glucose, mannose, and dextrin); chelating agents (e.g., EDTA); sugar alcohols (e.g., mannitol and sorbitol); salt-forming counterions (e.g., sodium); and non-ionic surfactants (e.g., polyoxyethylene sorbitan ester (Tween (trademark)), polyoxyethylene-polyoxypropylene block copolymers (Pluronic (trademark)), and polyethylene glycol).

To the medium to be used for the embryo preservation, one or more of known buffer salt solutions such as bicarbonate buffer, phosphate buffer, and modified solutions thereof; antibiotics; and the like; may be added, if necessary.

The mammalian embryos or fertilized eggs can be provided by a known method known in the art. For example, follicular eggs collected by aspiration from the ovary of a mammal may be cultured in vitro, and then be co-cultured with sperm of the same mammal (insemination) to obtain a fertilized egg, followed by developing the fertilized egg to obtain an embryo. In general, from the morphological viewpoint, embryos commercially distributed are at a stage between the morula stage and the blastocyst stage. Those skilled in the art can easily identify embryos at a stage between the morula stage and the blastocyst stage based on their morphologies. For example, such embryos can be easily identified by comparing their micrographs with the images provided in the International Embryo Transfer Society (IETS) manual.

The container for preservation of the embryo or fertilized egg may be any container as long as the container shows no toxicity to mammalian embryos or fertilized eggs, and examples of the container include straws for freezing semen, straws for fertilized egg implantation, sampling tubes, cryotubes, cell culture dishes, cell culture plates, and vials. For maintenance of a non-freezing low-temperature environment, a thermostat, thermostat container, incubation container (whose type may be either the gas (normally air) tank type or liquid (normally water) tank type), incubation bag, low-temperature chamber, household refrigerator, or the like may be used. Although light is preferably eliminated as much as possible during the preservation of the embryos or fertilized eggs, means commonly used for maintaining a non-freezing low-temperature environment usually provides a dark environment, and therefore in many cases no special care is required in this regard.

In the present invention, the mammalian embryo(s) or fertilized egg(s) is(are) enclosed in an appropriate preservation container in a state where the embryo(s) or fertilized egg(s) is(are) immersed in a medium containing serum and a Good's buffer at the specific concentrations described above, and the enclosed embryo(s) or fertilized egg(s) is(are) stored under a non-freezing low-temperature environment. The non-freezing low temperature means a low temperature at which the medium and the mammalian embryo(s) or fertilized egg(s) are not frozen, and examples of the non-freezing low temperature include temperatures within the range of −1 to 15° C., 2 to 10° C., or 4 to 5° C.

By the method of the present invention, a mammalian embryo(s) or fertilized egg(s) can be preserved at non-freezing low temperature for as long as 7 days without use of a cell life prolonging peptide such as mature Nfe11. For example, in the Examples below, it was found that the embryo preservation performance (the survival rate, hatching rate, and conception rate after the preservation) is especially excellent when medium 199 containing 50% (v/v) fetal bovine serum and, as the Good's buffer, 25 mM or 50 mM HEPES, is used. Thus, examples of especially preferred modes of the method of the present invention include, but are not limited to, a mode in which 45 to 55% (v/v) serum and, as the Good's buffer, 22.5 to 52.5 mM HEPES are used.

The medium containing serum and a Good's buffer at the specific concentrations described above to be used for the preservation method of the present invention may be provided as a preservative solution for preserving a mammalian embryo(s) or fertilized egg(s) at non-freezing low temperature. That is, the present invention also provides a preservative solution for a mammalian embryo(s) or fertilized egg(s), which preservative solution essentially consists of a medium containing 20 to 80% (v/v) serum and 10 to 100 mM Good's buffer.

In the present invention, since the long-term preservation at non-freezing low-temperature is achieved by a combination of serum and a Good's buffer at specific concentrations, there is no need to add a peptide having cell life prolonging activity to the medium. An example of the mode of the preservative solution of the present invention is a preservative solution essentially consisting of a medium which contains 20 to 80% (v/v) serum and 10 to 100 mM Good's buffer but contains neither (a) nor (b) described below.

(a) The peptide whose amino acid sequence is shown in SEQ ID NO:2

(b) A peptide having an identity of not less than 80% to the amino acid sequence shown in SEQ ID NO:2 and having cell life prolonging activity.

The term "essentially consisting of" means that any other component(s) may be contained as long as the component(s) do(does) not affect the effect of the invention. The preservative solution of the present invention may contain an arbitrary component(s) other than the peptide having cell life prolonging activity, as long as the medium contains serum at a specific concentration and a Good's buffer at a specific concentration. The component(s) that may be arbitrarily contained is(are) as described above. Preferred conditions in terms of the serum concentration, type of the serum, concentration of the Good's buffer, and the like are also as described above.

The preservative solution may be sterilized, as necessary, by filtration (normally with a filter having a pore size of 0.2 μm) or the like after its preparation, and stored in a cool and dark place until use.

EXAMPLES

The present invention is described below more concretely by way of Examples. However, the present invention is not limited to the Examples below.
<Materials and Methods>
1. Preparation of Bovine Embryos Embryos collected from donor bovine animals of Japanese Black Cattle and Holstein Cattle after superovulation were evaluated for their qualities according to the regulation by International Embryo Transfer Society (IETS manual. Manual of the international embryo transfer society. In: Stringfellow D A, Seidel S M, editors. Savoy, Ill., USA: IETS 1998). Low-quality embryos were subjected to an in vitro culture test after 7 days of non-freezing preservation, and high-quality embryos were subjected to investigation of the conception rate after implantation to recipient cattle.

Preservation of bovine embryos was carried out as follows (FIG. 1). First, a preservative solution alone was sucked into a straw having a capacity of 0.25 ml, and, after introduction of an air layer, a bovine embryo contained in the preservative solution was sucked. Thereafter, an air layer was introduced, and the preservative solution alone was sucked again. The straw was then sealed. Subsequently, the straw containing the sucked bovine embryo was immersed in water contained in a plastic container (plastic tube) which had been preliminarily cooled to 4 to 5° C. The plastic container was then stored in a refrigerator for 7 days at 4 to 5° C.

After the non-freezing preservation, the bovine embryo was washed 3 times by immersion in PBS(+) containing 5% (v/v) fetal bovine serum (FBS). The washed bovine embryo was cultured under 5% $CO_2$ at 38° C. in CR1aa medium containing 5% (v/v) FBS for 48 hours. Morphological observation was carried out under a stereoscopic microscope, and the embryo was judged to be alive if the progress of cleavage by the culture could be found and the cytoplasmic membrane was not disrupted. Live cells were checked for whether hatching from the zona pellucida could be observed or not. A bovine embryo washed with PBS(+) containing 5% (v/v) FBS was nonsurgically implanted into the deep part of the corpus-luteum-side uterine horn of each recipient cattle on Day 6 to 8 of an estrous cycle (the date of estrus was defined as Day 0). On Days 30 and 60 of the estrous cycle, pregnancy diagnosis was carried out. For a significance test to verify the effect of the embryo preservation solution according to the present invention, a $\chi^2$ test was used.

2. Preparation of Non-Freezing Preservative Solutions

To medium 199 (Invitrogen) supplemented with antibiotics (penicillin G potassium and streptomycin sulfate), FBS was added to 20 to 50% (v/v), and HEPES was also added to a concentration of 0 to 100 mM. In the conception test, a group in which a special peptide having a protection effect against low temperature (mature Nfe11, SEQ ID NO:2) was added was also provided. In addition, in order to investigate the effects of other Good's buffers other than HEPES, preservation solutions were prepared by adding FBS and a Good's buffer (PIPES or MOPS) to medium 199 such that the concentration of FBS was 50% (v/v) and the concentration of the Good's buffer was 25 mM. These preservation solutions were sterilized by filtration through a filter having a pore size of 0.2 μm, and stored in a refrigerator until use.

The special peptide (mature Nfe11) was prepared according to the following procedure.

According to the procedure described in Patent Document 1, a DNA sequence (SEQ ID NO:1) encoding mature Nfe11 (SEQ ID NO:2) was incorporated into pET20b (Novagen) to construct a plasmid pET20NFE11, and *E. coli* BL21 (DE3) (Novagen) was transformed with the resulting expression vector. The obtained transformant was cultured in 2×YT medium supplemented with 100 μg/ml ampicillin at 28° C. for 24 hours with shaking.

After the shake culture for 24 hours, 1/100 volume of the culture was subcultured into freshly prepared 2×YT medium supplemented with 100 μg/ml ampicillin, and shake culture was carried out at 28° C. When the turbidity of the culture reached $O.D._{600}$=0.5, IPTG (isopropyl-β-D(−)-thiogalactopyranoside) was added to the culture to a final concentration of 0.5 mM to induce expression of Nfe11, and culture was carried out for additional 18 hours.

The culture was then subjected to centrifugation at 5000 rpm for 15 minutes at 4° C. to collect the bacterial cells. To the collected cells, 1/20 volume, with respect to the volume of the culture, of TE buffer (10 mM Tris-HCl/1 mM EDTA, pH 8.0) was added, and PMSF (phenylmethylsulfonyl fluoride) was added to the resulting mixture to 0.1 mM, followed by suspending the bacterial cells.

The resulting suspension was once frozen and then thawed, followed by carrying out homogenization of the bacterial cells by an ultrasonic device. The obtained homogenate was subjected to centrifugation at 11,000 rpm for 20 minutes at 4° C., and the supernatant was collected. In this supernatant, citric acid monohydrate (13.2 g/L) and sodium chloride (29.2 g/L) were dissolved, and the resulting solution was left to stand at 4° C. for 1 hour. Thereafter, the precipitate generated was subjected to centrifugation at 6,000 rpm at 4° C. for 30 minutes, and a supernatant containing the protein of interest was collected.

The supernatant containing the protein of interest described above was passed through a Sephadex G-25 gel filtration column (GE Healthcare) with an inner diameter of 5.0 cm and a height of 26 cm (capacity, 500 ml) using 5 mM sodium citrate solution as the mobile phase, to obtain a protein solution in which the solvent was replaced with 5 mM sodium citrate solution. Subsequently, the pH of the protein solution was adjusted to 2.9 with a citric acid solution, and the solution was then left to stand at 4° C. overnight to allow acid denaturation and precipitation of contaminating proteins. The resulting precipitate was removed by centrifugation at 6,000 rpm at 4° C. for 30 minutes, to obtain a supernatant containing the protein of interest.

Thereafter, a cation exchange High-S column (Bio-Rad) with an inner diameter of 5.0 cm and a height of 4.6 cm (capacity, 90 ml) was preliminarily equilibrated with 50 mM sodium citrate buffer (pH 2.9), and the collected supernatant containing the protein of interest was passed through the column. The protein of interest adsorbed to the resin was eluted with 50 mM sodium citrate/330 mM NaCl (pH 2.9), and collected. The aqueous solution of the purified product was further subjected to 5 times of dialysis with 10 volumes of ultrapure water, and then subjected to freeze drying, thereby obtaining freeze-dried powder of the purified product of mature Nfe11.

<Results and Discussion>

1. Preservation Effect of HEPES-Containing Preservation Solutions on Embryos

As shown in Table 1, it was found that low-quality bovine embryos preserved in a non-freezing preservative solution whose HEPES concentration was adjusted to 12.5 to 100 mM showed a higher survival rate after preservation for 7 days compared to the HEPES-free group. The rate of hatching from the zona pellucida was especially high in the cases where the preservative solution contained HEPES at a concentration of 25 to 50 mM and FBS at a concentration of 50% (v/v).

TABLE 1

Survival rate of bovine embryos preserved for 7 days in the non-frozen state in medium 199 containing HEPES and FBS

| HEPES concentration | FBS concentration | Number of tested embryos | Number of live embryos (%) | Number of hatched embryos (%) | pH upon completion of preservation |
|---|---|---|---|---|---|
| 0 mM | 20% | 30 | 4(13.3)$^a$ | 1(3.3)$^a$ | 7.9 |
| | 50% | 30 | 3(10.0)$^a$ | 1(3.3)$^a$ | 7.7 |
| 12.5 mM | 20% | 35 | 9(25.7)$^a$ | 3(8.6)$^{ab}$ | 7.4 |
| | 50% | 35 | 19(54.3)$^b$ | 9(25.7)$^{bc}$ | 7.4 |

TABLE 1-continued

Survival rate of bovine embryos preserved for 7 days in the non-frozen state in medium 199 containing HEPES and FBS

| HEPES concentration | FBS concentration | Number of tested embryos | Number of live embryos (%) | Number of hatched embryos (%) | pH upon completion of preservation |
|---|---|---|---|---|---|
| 25 mM | 20% | 36 | 23(63.9)$^b$ | 9(25.0)$^{bc}$ | 7.3 |
| | 50% | 36 | 25(69.4)$^b$ | 13(36.1)$^c$ | 7.0 |
| 50 mM | 20% | 30 | 19(63.3)$^b$ | 8(26.7)$^{bc}$ | 6.9 |
| | 50% | 30 | 22(73.3)$^b$ | 10(33.3)$^c$ | 6.8 |
| 100 mM | 50% | 20 | 13(65.0)$^b$ | 4(20.0)$^{abc}$ | 6.9 |

$a, b, c$ difference is significant between different symbols (P < 0.05)

While the pH of the non-freezing preservative solution containing HEPES was within the range of 6.9 to 7.4 upon completion of the preservation, the pH in the HEPES-free group was 7.7 to 7.9. It is said that the optimum pH for cells is usually 6.8 to 7.2, and that cells can be ideally maintained within this pH range. HEPES, which is a Good's buffer, is known to have high buffer capacity and high solubility in aqueous solutions to stabilize the pH. It has been thought that Good's buffers do not easily pass through the cell membrane. In view of this, the protection effect of tris (hydroxymethyl)aminomethane (hereinafter referred to as tris), which is often used as a buffer together with HEPES and is not a Good's buffer, against low temperature was studied by low-temperature preservation of bovine embryos in medium 199 containing 50% (v/v) FBS supplemented with 25 mM tris (whose pH was adjusted to 7.2 with hydrochloric acid) for 7 days. As a result, the survival rate and the hatching rate after the preservation were very low: 10.0% and 5.0%, respectively. The pH after the low-temperature preservation was 7.2. These results suggested that, although HEPES has an effect to stabilize the pH of the non-freezing preservative solution, the improvement of the performance in the non-freezing preservation of embryos may not be significantly dependent on the stabilization per se of the pH, but may be based on a cell-membrane-protecting effect, other than the pH stabilization effect, of HEPES during the low-temperature preservation.

2. Investigation of Conception Ability

Subsequently, the conception ability of high-quality bovine embryos that had been preserved in the non-frozen state for 7 days was investigated. Since the concentration of HEPES generally recommended for use in cell culture is 10 to 25 mM (Luo S et al., Effect of HEPES buffer on the uptake and transport of P-glycoprotein substrates and large neutral amino acids. Mol Pharm 2010; 7:412-420), the concentration of HEPES in the non-freezing preservative solution used in the present test for investigation of the conception ability was set to 25 mM. The special recombinant peptide having a protection effect against low temperature (mature Nfe11 peptide) was added to medium 199 containing 50% (v/v) FBS supplemented with 25 mM HEPES, to see whether the peptide improves the conception ability or not. The results are shown in Table 2.

TABLE 2

Conception rate of bovine embryos preserved for 7
days in the non-frozen state in medium 199 containing
50%(V/V) FBS supplemented with 25 mM HEPES

| Special recombinant peptide | Number of implanted embryos | Conceptus number on Day 30 (%) | Conceptus number on Day 60 (%) |
|---|---|---|---|
| Not contained | 16 | 12 (75.0) | 12 (75.0) |
| Contained | 16 | 12 (75.0) | 12 (75.0) |

The conception rate of the high-quality bovine embryos preserved in the non-frozen state for 7 days in the medium 199 containing 50% (v/v) FBS supplemented with 25 mM HEPES was as high as 75.0%. Death of early embryos was not found between Day 30 and Day 60 of pregnancy, and birth of normal calves could be observed. No conception-promoting effect was found in the special peptide in the present study. The results of the present study indicate that the effect of the special recombinant peptide can be substituted by use of HEPES and serum.

3. Investigation of Effects of Good's Buffers Other Than HEPES

In order to investigate the effects of Good's buffers other than HEPES, the following experiment was carried out using, in addition to HEPES, the Good's buffers shown in Table 3 below.

Using medium 199 to which a Good's buffer was added at 25 mM (FBS concentration, 50% (v/v) FBS), bovine embryos were preserved at low temperature for 7 days, and the survival rate and the hatching rate were investigated by the method described above. As a control, medium 199 which does not contain a Good's buffer and contains FBS at a concentration of 50% (v/v) was used. The results are shown in Table 3. In Table 3, "pH" indicates the pH of the medium upon completion of the refrigerated storage for 7 days.

TABLE 3

| Buffer | N | Survival rate (%) | Hatched embryos (%) | pH |
|---|---|---|---|---|
| TES | 20 | 6(30.0) | 3(15.0) | 7.2 |
| PIPES | 20 | 8(40.0) | 5(25.0) | 7.0 |
| MOPS | 20 | 9(45.0) | 5(25.0) | 7.0 |
| EPPS | 20 | 7(35.0) | 2(10.0) | 7.3 |
| HEPES | 36 | 25(69.4) | 13(36.1) | 7.0 |
| Not added | 30 | 3(10.0) | 1(3.3) | 7.7 |

Also in the cases where a Good's buffer other than HEPES was used, the survival rate and the hatching rate of the embryos after the preservation for 7 days tended to be high. Although HEPES had the highest effect, the Good's buffers other than HEPES could also be confirmed to have the effect to protect embryos during non-freezing low-temperature preservation.

DESCRIPTION OF SYMBOLS

10 Bovine embryo
12 Preservative solution
14 Straw
16 Plastic Tube
18 Air layer
20 Water

The invention claimed is:

1. A method for preserving a mammalian embryo(s) or fertilized egg(s), said method comprising:
   immersing a mammalian embryo(s) or fertilized egg(s) in a medium containing 30 to 80% (v/v) serum and 12.5 to 100 mM HEPES, and
   storing the embryo(s) or fertilized egg(s) at a non-freezing low temperature between −1 to 15° C.,
   wherein said embryo(s) or fertilized egg(s) is/are not frozen during the entirety of said method and have not ever undergone freezing.

2. The method according to claim 1, wherein said medium is a medium which does not contain a peptide having cell life prolonging activity.

3. The method according to claim 1, wherein said medium does not contain a peptide whose amino acid sequence is shown in SEQ ID NO:2 or is a peptide having an identity of not less than 95% to the amino acid sequence shown in SEQ ID NO:2.

4. The method according to claim 1, wherein the serum concentration is 45 to 55% (v/v).

5. The method according to claim 1, wherein the serum concentration is 30 to 60% (v/v).

6. The method according to claim 1, wherein the HEPES concentration is 22.5 to 52.5 mM.

7. The method according to claim 1, wherein the HEPES concentration is 20 to 80 mM.

8. The method according to claim 1, wherein said serum is bovine serum.

9. The method according to claim 1, wherein said mammal is cattle.

10. The method according to claim 1, wherein said non-freezing low temperature is a temperature of 2 to 10° C.

11. The method according to claim 1, wherein said embryo(s) is(are) an embryo(s) at a stage between the morula stage and the blastocyst stage.

12. The method according to claim 1, wherein the embryo(s) or fertilized egg(s) is/are stored for a period of time where at least some of said embryo(s) or fertilized egg(s) remain alive at said non-freezing low temperature.

13. The method according to claim 1, wherein the embryo(s) or fertilized egg(s) is/are stored at said non-freezing low temperature for a period of days up to 7 days.

14. The method according to claim 2, wherein said peptide is a peptide whose amino acid sequence is shown in SEQ ID NO:2.

15. The method according to claim 12, wherein the embryo(s) or fertilized egg(s) is/are stored at said non-freezing low temperature for a period of days up to 7 days.

* * * * *